(12) United States Patent
Isak et al.

(10) Patent No.: US 6,693,191 B2
(45) Date of Patent: Feb. 17, 2004

(54) METHOD FOR THE PRODUCTION OF A PARTICLE-CONTAINING PREPARATION OF TETRAHYDRO-3,5-DIMETHYL-1,3,5-THIADIAZIN-2-THIONE

(75) Inventors: Heinz Isak, Böhl-Iggelheim (DE); Norbert Sendhoff, Wachenheim (DE); Franz Schütz, Neustadt (DE); Jörg Therre, Worms (DE); Michael Drögemüller, Uelzen (DE); Dirk Franke, Ludwigshafen (DE); Manfred Munzinger, Dirmstein (DE); Alexander Weck, Freinsheim (DE); Kirsten Burkart, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/343,973

(22) PCT Filed: Aug. 16, 2001

(86) PCT No.: PCT/EP01/09471
§ 371 (c)(1),
(2), (4) Date: Feb. 6, 2003

(87) PCT Pub. No.: WO02/14296
PCT Pub. Date: Feb. 21, 2002

(65) Prior Publication Data
US 2003/0176692 A1 Sep. 18, 2003

(30) Foreign Application Priority Data
Aug. 17, 2000 (DE) ........................... 100 40 194.5

(51) Int. Cl.$^7$ .............................................. C07D 285/34
(52) U.S. Cl. .......................................................... 544/8
(58) Field of Search ............................................... 544/8

(56) References Cited

U.S. PATENT DOCUMENTS

| 2,838,389 A | 6/1958 | Yoder | 544/8 |
| 5,495,017 A | 2/1996 | Appler | 544/8 |

OTHER PUBLICATIONS

Derwent Abst. DD 289 055 not complete.
Abst. H3009 incomplete citation.
XP–002183831 incomplete citation.
XP–002173732 incomplete citation.

*Primary Examiner*—John M. Ford
(74) *Attorney, Agent, or Firm*—Keil & Weinkauf

(57) ABSTRACT

Described is a process for the preparation of a particulate tetrahydro-3,5-dimethyl-1,3,5-thiadiazine-2-thione product by combining a first aqueous solution comprising methylammonium N-methyldithiocarbamate with a second aqueous solution comprising formaldehyde, followed by separation and drying of the resulting solid, which comprises combining the first and the second aqueous solutions in such a way that the ratio between the concentrations of dithiocarbamate functions and of formaldehyde is essentially constant in the reaction mixture over time during the duration of the reaction.

10 Claims, No Drawings

METHOD FOR THE PRODUCTION OF A PARTICLE-CONTAINING PREPARATION OF TETRAHYDRO-3,5-DIMETHYL-1,3,5-THIADIAZIN-2-THIONE

The present invention relates to a process for the preparation of a particulate tetrahydro-3,5-dimethyl-1,3,5-thiadiazine-2-thione product by combining a first aqueous solution comprising methylammonium N-methyldithiocarbamate with a second aqueous solution comprising formaldehyde, followed by separation and drying of the resulting solid.

Tetrahydro-3,5-dimethyl-1,3,5-thiadiazine-2-thione, which is also known under the common name dazomet, is employed in agriculture and horticulture for soil sterilization, i.e. for controlling nematodes, germinating plants and cell fungi (cf. U.S. Pat. No. 2,838,389). The action is based on the slow release of methyl isothiocyanate in the soil by hydrolytic and/or enzymatic breakdown of tetrahydro-3,5-dimethyl-1,3,5-thiadiazine-2-thione.

To avoid the formation of aerosols, which are a potential health hazard, during packaging, handling and/or applying the active ingredient, a particulate tetrahydro-3,5-dimethyl-1,3,5-thiadiazine-2-thione product is desirable whose fines, with particle sizes of less than 100 $\mu$m, amount to as little as possible. On the other hand, the particulate product should also not contain a substantial proportion of coarse particles with particle sizes of over 400 $\mu$m in order to guarantee sufficiently rapid decomposition of the active ingredient in the soil. The known preparation processes of tetrahydro-3,5-dimethyl-1,3,5-thiadiazine-2-thione only allow the preparation of particulate tetrahydro-3,5-dimethyl-1,3,5-thiadiazine-2-thione products with an inadequately homogeneous particle size distribution.

WO 93/13085 describes a process for the preparation of tetrahydro-3,5-dimethyl-1,3,5-thiadiazine-2-thione granules by reacting the methylammonium salt of N-methyldithiocarbamic acid with formaldehyde in the presence of a diaminoalkylene. Under the reaction conditions, the diaminoalkylene leads to the formation of products which act as crystallization inhibitors and which, together with the crystallites of the active ingredient, form a random conglomerate. WO 93/13085 recommends adding the methylammonium N-methyldithiocarbamate solution to an aqueous formaldehyde solution. It has emerged that reproducible particle size distributions can only be obtained by the known process when a large number of parameters, including the rate at which the reactants are added, the intensity of mixing the reactants, the mixing time and the like, are observed accurately. The preparation of a product with constant properties and of flexible response to varying demands is thus made difficult.

It is an object of the present invention to provide a process for the preparation of a particulate tetrahydro-3,5-dimethyl-1,3,5-thiadiazine-2-thione product which, despite simple process control, yields products with a narrow particle size distribution, in particular with a reduced content of fines of a particle size of less than 100 $\mu$m.

This object is achieved according to the invention by a process for the preparation of a particulate tetrahydro-3,5-dimethyl-1,3,5-thiadiazine-2-thione product by combining a first aqueous solution comprising methylammonium N-methyldithiocarbamate with a second aqueous solution comprising formaldehyde, followed by separation and drying of the resulting solid, which comprises combining the first and the second aqueous solutions in such a way that the ratio between the concentrations of dithiocarbamate functions and of formaldehyde is essentially constant in the reaction mixture over time.

The invention furthermore relates to a particulate agrotechnical product with a tetrahydro-3,5-dimethyl-1,3,5-thiadiazine-2-thione content of at least 95% by weight and such a particle size distribution that less than 7% by weight, preferably less than 3% by weight, of the particles have a particle diameter of less than 100 $\mu$m, over 50% by weight of the particles have a particle diameter of less than 200 $\mu$m, over 90% by weight of the particles have a particle diameter of less than 300 $\mu$m, and over 95% by weight of the particles have a particle diameter of less than 400 $\mu$m.

The particulate product obtained in accordance with the invention preferably has a bulk density of 0.4 to 0.8 kg/l, in particular 0.6 to 0.7 kg/l.

It has been found that narrow particle size distributions can be obtained when the first and the second aqueous solutions are combined in such a way that the ratio between the molar concentration of dithiocarbamate function and formaldehyde in the reaction mixture is essentially constant over the duration of the reaction.

The process according to the invention thus differs essentially from the known processes, in which a reactant, as a rule the aqueous formaldehyde solution, is introduced into the reaction vessel and the other reactant is metered in over a period of time. It can be seen that, in the known processes, the reactant which has initially been introduced is present in a multiple molar excess at the beginning of the metering-in operation. The ratio between the reactant which has initially been introduced and the reactant which is metered in then decreases constantly over the duration of the metering-in operation.

The process according to the invention can be carried out semicontinuously or continuously. To this end, it is expedient to introduce essentially stoichiometrically equivalent amounts of the first aqueous solution, calculated as dithiocarbamate functions, and of the second aqueous solution, calculated as formaldehyde, i.e. essentially twice the molar amount of formaldehyde, into a reaction space per unit time. An "essentially stoichiometrically equivalent" amount is such an amount which is within 20%, preferably within 10%, of the stoichiometrically required amount of the reactant in question. It is also possible to introduce an amount greater than the stoichiometrically required amount of a reactant if the accumulation, in the reaction mixture, of the reactant employed in excess is prevented by suitable measures. For example, the accumulation can be prevented by continuously removing the excess, for example by continuously discarding some of the mother liquor which is obtained when the product is removed from the reaction mixture, as is illustrated in further detail hereinbelow.

Reactors which are suitable for carrying out the reaction procedure continuously are customary reactors such as, in particular, a continuous stirred-vessel reactor or a stirred-vessel cascade. It is expedient to ensure good mixing of the reactants in the reaction space. The introduction of the first and/or second aqueous reaction solution can be carried out for example in such a way that some of the reaction mixture is continuously removed from the reaction space, mixed with the first and/or second aqueous reaction solution and recirculated into the reaction space. Removal, mixing and recirculating are effected for example by pumping the reaction mixture via a metering and mixing section into which the first and/or second solution are fed. Instead of stirred-vessel reactors or stirred-vessel cascades, tubular reactors which are optionally provided with elements like static mixers may also be used.

Sparingly soluble tetrahydro-3,5-dimethyl-1,3,5-thiadiazine-2-thione is formed as aqueous suspension when the aqueous solutions are combined. When the process according to the invention is carried out continuously, suspension is continuously withdrawn from the reaction space or, when using a reactor cascade, from the last reactor of the cascade. The solid is separated from the resulting suspension by customary processes, for example by filtration or centrifugation. Suitable devices, such as pressure filters, vacuum filter belts, rotary drum type filters and centrifuges, are known to those skilled in the art. All or some of the mother liquor which remains can be recirculated or eliminated from the process. An accumulation of contaminants or of reactants employed in excess can be prevented in the system by discharging at least some of the mother liquor.

The solid which has been separated off from the mother liquor can be washed, for example with cold or warm water. To this end, the solid can be made into a slurry with the wash medium and subsequently be separated off.

The solid which has been separated off from the mother liquor and, if appropriate, washed can then be dried by customary methods. Pneumatic conveyor dryers or fluidized beds are suitable for this purpose.

In some cases, it may be advantageous to mix the moist cake obtained after the mother liquor has been removed with material which has already been dried and to subject the mixture to further drying in order to prevent caking during drying. When the process is carried out continuously, this can be achieved by recirculating some of the dried material.

It is preferred to combine the first and second aqueous solutions in the presence of seed crystals of tetrahydro-3,5-dimethyl-1,3,5-thiadiazine-2-thione. The addition of seed crystals additionally allows the influencing of the particle size distribution and/or bulk density of the resulting particulate product. The material used as seed crystals is finely divided tetrahydro-3,5-dimethyl-1,3,5-thiadiazine-2-thione, for example in an amount of 1.5 mol % to 10 mol %, preferably 2.5 mol % to 7.5 mol %, in particular 3 mol % to 6 mol %, based on the methylammonium N-methyldithiocarbamate employed. Seed crystals with a particle size of less than 100 $\mu$m are preferably used. Usually, 90% of the seed crystals should have a particle size of between 50 and 5 $\mu$m. Particularly preferred is a particle size distribution of the seed crystals in which 100% of the particles are smaller than 100 $\mu$m, approximately 90% are between 50 and 1 $\mu$m and approximately 10% are less than 5 $\mu$m.

To achieve as uniform as possible a distribution of the seed crystals in the reaction mixture, the seed crystals are preferably added to the reaction mixture in the form of an aqueous suspension.

Seed crystals of a desired particle size can be obtained by comminuting, for example grinding, tetrahydro-3,5-dimethyl-1,3,5-thiadiazine-2-thione which has been prepared beforehand. In a possible embodiment of the invention, seed crystals of a suitable size are obtained by subjecting the particulate solid removed from the reaction space to sizing, resulting in fines and in course particles, the fines being recirculated into the reaction space as seed crystals and the coarse particles being discharged from the process as product. Sizing can be carried out both in the suspended state and in the dry state. To carry out the sizing operation in the dry state, the solid is beforehand separated from the mother liquor and dried. The fines obtained can be suspended in an aqueous medium to be recirculated into the reaction space. Suitable devices for sizing are, for example, hydrocyclones and wet screens for screening suspended particles, and cyclones, sieves or screens for screening dried particles.

To prepare the first aqueous solution, a procedure is generally followed in which an aqueous solution of methylamine, if appropriate with the concomitant use of an alkylenediamine such as described hereinbelow, is first treated with carbon disulfide. The reaction of the aqueous methylamine solution, if appropriate with the concomitant use of an alkylenediamine, with carbon disulfide can be carried out continuously, semicontinuously or batchwise. The continuous reaction can be carried out in any reactors which are suitable for this purpose, for example reaction towers or jet-loop reactors, preferably in stirred vessels. To achieve as complete reaction as possible, it is recommended to use a cascade of reactors composed of at least one main reactor and a secondary reactor.

To prepare the first aqueous solution, it is preferred to use an excess of carbon disulfide. Unreacted carbon disulfide separates from the aqueous solution of the dithiocarbamate, being the phase with the greater specific weight. It has proved advantageous to remove the unreacted carbon disulfide to less than 0.5% by weight, and particularly less than 0.3% by weight, especially preferably less than 0.1% by weight, based on the first aqueous solution, before combining the latter with the second aqueous solution. Greater amounts of excess carbon disulfide tend to form finely dispersed droplets which interfere with the precipitation process in the subsequent reaction with the aqueous formaldehyde solution owing to flotation and which, undesirably, can lead to the increased formation of ultrafine particles with a size of less than, for example, 10 $\mu$m. Separation of the unreacted carbon disulfide can be achieved for example by settling and subsequent phase separation. For settling, the mixture of aqueous carbamate solution and unreacted carbon disulfide can be passed into a calming zone. This is expediently effected in a continuously operated phase separation vessel in horizontal position through which a slow flow is passed. Owing to the different densities of the phases, the emulsion separates in the field of gravitation so that the two phases are present coherently and essentially without foreign phases one above the other.

A disadvantage of largely removing the carbon disulfide phase are the very long settling times. In order to achieve more rapid phase separation, one or more coalescence levels with an integrated phase separation device or a phase separation device which is arranged downstream are advantageously used. Generally suitable are separators with coalescence devices such as packing material, coalescence faces or fine-celled elements over which or through which the emulsion to be separated must flow. If appropriate, most of the unreacted carbon disulfide is first removed, and the aqueous solution, which still comprises finely dispersed carbon disulfide droplets, is passed through an apparatus with coalescence-promoting devices and the coalesced carbon disulfide phase is separated off.

As a rule, the devices with coalescence phases are stacks of sheets with corrugated or oblique faces to which dispersed droplets adhere and initially form a film. When this film covers the individual sheet and is sufficiently thick, large drops of the dispersed phase form at the edge of the sheet and drop downward. They subsequently form a layer in the separator which can be separated readily by mechanical means. In the case of fine-celled devices, the internal structure of the elements forces the finely dispersed drops to come into contact with the internal surface and they then form a film and leave the hollow structure of the fine-celled elements as combined larger drops. Packing material which is suitable is packing material conventionally used in distillation. The emulsion to be separated is preferably passed through a bed of packing material. Wetting of the large surface of the packaging material results in surface coalescence and simultaneously drop-to-drop coalescence, owing to the movement of the drops.

Porous devices in the form of filter cartridges composed of, for example, porous polypropylene, have proved advantageous. A mean pore size of the porous devices of less than 50 μm is particularly suitable.

Since not only the reaction of carbon disulfide with methylamine, but also the reaction of methylammonium N-methyldithiocarbamate with formaldehyde, is exothermic, while the intermediate and the product are sensitive to high temperatures, it is recommended to carry out the reaction with cooling. In general, the reactions proceed at a sufficient rate above 10° C., while temperatures above 50° C. increasingly lead to the formation of undesired byproducts. The reactions are therefore usually carried out at a temperature of 20 to 40° C.

In preferred embodiments of the process according to the invention, the first aqueous solution comprises, in addition to methylammonium N-methylthiocarbamate, at least one alkylenediamine and/or reaction products thereof with carbon disulfide. The first aqueous solution expediently comprises 0.1 to 10 mol %, preferably 0.2 to 5 mol %, in particular 0.5 to 1.5 mol %, of alkylenediamine, based on the amount of methylamine on which it is based. Suitable alkylenediamines have the formula I

$R^1$—NH-A-NH—$R^2$      (I)

in which $R^1$ and $R^2$ independently of one another are hydrogen or the compound $C_1$–$C_4$-alkyl and A is straight-chain or branched $C_2$–$C_8$-alkylene, preferably 1,2-ethylene, 1,2-propylene, 1,3-propylene or 1,4-butylene.

Preferred alkylenediamines are those mentioned in WO 93/13085. Preferred among these are ethylenediamine, 1-(N-methylamino)-2-aminoethane, 1,2-di(N-methylamino) ethane, 1,2-diaminopropane, 1,2-di(N-methylamino) propane and 1-(N-methylamino)-2-aminopropane. Ethylenediamine is especially preferred. The pure compounds, but also mixtures of these compounds, may be employed.

The use of alkylenediamines with two primary amino groups, for example those of the above formula I in which $R^1$=$R^2$=H, in particular ethylenediamine, is preferred. It has emerged that particularly advantageous particle size distributions are obtained when the alkylenediamine and its possible reaction products with carbon disulfide, i.e. its reaction product with 1 mol of carbon disulfide (N-aminoalkyldithiocarbamate) and its reaction product with 2 moles of carbon disulfide (alkylene-N,N'-bis (dithiocarbamate)), are present in a particular molar ratio to each other in the first aqueous solution. The first aqueous solution preferably comprises alkylenediamine, N-aminoalkyldithiocarbamate and alkylene-N,N'-bis (dithiocarbamate) in a molar ratio of 1:0.5:0.5 to 1:10:10, in particular 1:1:1 to 1:10:6. The free amino functions of the alkylenediamine or of its reaction products with 1 mol of carbon disulfide can be in protonated form; as a rule, the dithiocarbamate functions are present as N-methylammonium salt or as internal salt together with an ammonium group present within the same molecule. The molar ratio of alkylenediamine and its reaction products with carbon disulfide is preferably determined indirectly by analyzing the products obtained after the reaction of the first and the second aqueous solutions. Thus, an alkylenediamine of the formula I where $R^1$=$R^2$=H reacts with 2 moles of N-methyldithiocarbamate and 4 moles of formaldehyde to give (1), N-aminoalkyldithiocarbamate with 1 mol of N-methyldithiocarbamate, 1 mol of methylammonium ions and 4 moles of formaldehyde to give (2), and alkylene-N,N'-bis(dithiocarbamate) with 2 moles of N-methylammonium ions and 4 moles of formaldehyde to give (3).

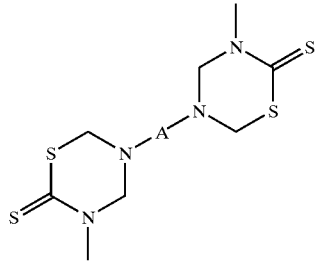

(1)

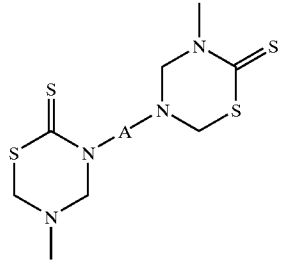

(2)

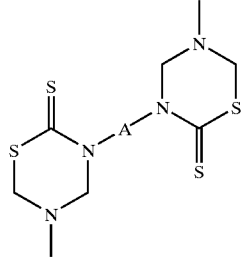

(3)

The products (1), (2) and (3) can suitably be separated from the product obtained (in addition to the main component tetrahydro-3,5-dimethyl-1,3,5-thiadiazine-2-thione) and determined quantitatively by means of high-performance liquid chromatography.

The molar ratio of alkylenediamine and its reaction products with carbon disulfide in the first aqueous solution can be controlled by varying the sequence in which methylamine, carbon disulfide and alkylenediamine are combined and/or by varying the residence time prior to addition of a further reactant. Thus, to prepare the first aqueous solution, it is preferred first to react an aqueous solution of methylamine with carbon disulfide and to add the alkylenediamine to the resulting solution. Preferably, 60 to 95% of the reaction between methylamine and carbon disulfide has taken place at the point in time when the alkylenediamine is added. The reaction between methylamine and carbon disulfide can be monitored for example by sampling, monitoring the pH or monitoring the reaction enthalpy. When using a cascade of reactors for the preparation of the first aqueous solution, the alkylenediamine is preferably metered into the secondary reactor in order to adjust the abovementioned ratio between alkylenediamine and its reaction products with carbon disulfide.

It has proved advantageous to carry out the reaction of the first and the second aqueous solution in the presence of small amounts of electrolyte. This is achieved expediently by using not demineralized water, but tap water or river water, for preparing the first aqueous solution or for diluting the reaction mixture. The presence of small amounts of electrolyte presumably prevents electrostatic charging and agglomeration of the precipitated particles. In general, suitable amounts of electrolyte are those which correspond to a conductivity of 500 to 1000 μS/cm.

When carrying out the process according to the invention and/or preparing the methylammonium N-methylthiocarbamate solution, waste air is generally obtained which is contaminated with carbon disulfide, and official regulations and the like stipulate that this waste air cannot simply be released into the environment. The waste air loaded with carbon disulfide can be freed from carbon disulfide by adsorption onto suitable adsorbents such as active charcoal, or washing with basic liquids, for example aqueous sodium hydroxide or primary, secondary or tertiary amines. In a preferred embodiment, the waste gas is scrubbed with an aqueous methylamine solution, during which process methylammonium N-methyldithiocarbamate forms while eliminating most of the carbon disulfide from the waste air. The methylamine solution, which is loaded with some carbon disulfide, can then advantageously be used for preparing the first aqueous solution in the process according to the invention. Waste gas scrubbing with the methylamine solution used as starting material in the process according to the invention is preferably employed in a continuous process.

As an alternative, or additionally, waste gas scrubbing can be carried out with an alkylenediamine, either in the form of an aqueous solution or, if the alkylenediamine is sufficiently fluid at the treatment temperature, in substance. In accordance with a preferred embodiment of the process according to the invention, the alkylenediamine obtained during this process, which is loaded with some carbon disulfide, is then advantageously used for preparing the first aqueous solution comprising methylammonium N-methylthiocarbamate, as has been described above.

Traces of iron ions, which originate, for example, from corrosion of the containers used or which are present in the process water, can lead to undesired discolorations of the resulting tetrahydro-3,5-dimethyl-1,3,5-thiadiazine-2-thione. The color may be lightened by addition of chelating agents such as nitrilotriacetic acid, ethylenediaminetetraacetic acid, N-(2-hydroxyethyl)ethylenediaminetriacetic acid, diethylenetriaminepentaacetic acid, all of which can be employed in the form of the free acid or as the alkali metal salt, preferably the sodium salt. Addition of the complexing agent can take place at any desired point of the process according to the invention or during the reaction of methylamine with carbon disulfide, preferably during the reaction of carbon disulfide and methylamine. Suitable amounts are, for example, 0.05 to 0.5% by weight, based on the weight of the tetrahydro-3,5-dimethyl-1,3,5-thiadiazine-2-thione formed.

The invention is illustrated in greater detail by the examples and comparative examples which follow.

COMPARATIVE EXAMPLE A

Batchwise Precipitation 2530.1 g of water, 2476.8 g of 40% strength aqueous monomethylamine, 20.7 g of ethylenediamine and 1540.5 g of $CS_2$ were reacted per hour at 35° C. in a cascade composed of two 4 l reactors linked to each other via a barometric discharge. The suspension obtained was passed through a filter cartridge operated as coalescence filter. Following phase separation of excess $CS_2$, this gave 6351.8 g of methylammonium N-methyldithiocarbamate as 36.5% strength aqueous solution (residual $CS_2$ content approx. 0.05% by weight) per hour.

A 160 l reactor was charged, at 20° C., with 79.8 kg of water, 26.61 kg of 40% strength formaldehyde solution and 1.42 kg of seed material (mean particle size <50 μm), and a total of 61 kg of methylammonium N-methyldithiocarbamate were metered in in the course of 2 hours as 36.5% strength aqueous solution. After filtration, 27.4 kg of dazomet were obtained.

| Particle sizes: | 42.0% | <100 μm |
|---|---|---|
| | 98.4% | <200 μm |
| | 99.6% | <300 μm |
| | 99.8% | <400 μm |
| Bulk density: | 0.69 kg/l | |
| L value (UV-VIS): | 63.1 (determined by reflectometry, where 100 = complete reflection; 0 = complete absorption of standard light) | |

EXAMPLE B

Continuous Precipitation Without Seeding 1686.7 g of water, 1651.2 g of 40% strength aqueous monomethylamine, 11.1 g of ethylenediamine and 1027.0 g of $CS_2$ were reacted per hour at 35° C. in a cascade composed of two 4 l reactors linked to each other via a barometric discharge, the ethylenediamine being metered into the second reactor. The suspension was passed through a filter cartridge operated as coalescence filter. After phase separation of excess $CS_2$, this gave 4234.5 g of methylammonium N-methyldithiocarbamate per hour as 36.5% strength aqueous solution (residual $CS_2$ content approx. 0.05% by weight).

2301.2 g of methylammonium N-methyldithiocarbamate as 36.5% strength aqueous solution, 993.0 g of 40% strength formaldehyde solution and 3078.7 g of recirculated mother liquor were metered per hour at 25° C. into a 7 l reactor. Centrifugation gave 1146.7 g of dazomet with residual moisture.

| Particle sizes: | 0.1% | <100 μm |
|---|---|---|
| | 25.6% | <200 μm |
| | 91.6% | <300 μm |
| | 96.4% | <400 μm |
| Bulk density: | 0.49 kg/l | |
| The above compounds (1), (2) and (3) (where A = 1,2-ethylene) are present in the ratio 33:34:33. | | |
| L value (UV-VIS): | 77.0 | |

Addition of 3 g of the disodium salt of ethylenediaminetetraacetic acid per hour into the reaction of methylamine and carbon disulfide gave dazomet with a color value of 92.3.

EXAMPLE C

Continuous Precipitation with Seeding 57.7 kg of methylammonium N-methyldithiocarbamate as 36.5% strength aqueous solution prepared as described in Example B, 28.1 kg of 40% strength formaldehyde solution, 83.6 kg of water and 1.0 kg of seed material (mean particle size <50 μm) were reacted per hour in a 160 l reactor. The resulting dazomet had the following properties:

| | | |
|---|---|---|
| Particle sizes: | 6.8% | <100 μm |
| | 73.6% | <200 μm |
| | 95.6% | <300 μm |
| | 98.6% | <400 μm |
| Bulk density: | 0.68 kg/l | |

EXAMPLE D

Continuous Precipitation with Seeding 28.85 kg of methylammonium N-methyldithiocarbamate as 36.5% strength aqueous solution prepared as described in Example B, 14.05 kg of 40% strength formaldehyde solution, 41.8 kg of water and 0.1 kg of seed material (mean particle size <50 μm) were reacted per hour in a 160 l reactor. The resulting dazomet had the following properties:

| | | |
|---|---|---|
| Particle sizes: | 2% | <100 μm |
| | 50.4% | <200 μm |
| | 93.2% | <300 μm |
| | 96.8% | <400 μm |

We claim:

1. A process for the preparation of a particulate tetrahydro-3,5-dimethyl-1,3,5-thiadiazine-2-thione product by combining a first aqueous solution comprising methylammonium N-methyldithiocarbamate with a second aqueous solution comprising formaldehyde, followed by separation and drying of the resulting solid, which comprises combining the first and the second aqueous solutions in such a way that the ratio between the concentrations of dithiocarbamate functions and of formaldehyde is essentially constant in the reaction mixture over time during the duration of the reaction, and separating the solid from the resulting suspension.

2. The process as claimed in claim 1, wherein the mass flows of the first and of the second aqueous solution which are introduced simultaneously into the reaction space are such that stoichiometrically essentially equivalent quantities of dithiocarbamate functions and formaldehyde are introduced per unit time.

3. The process as claimed in claim 1, wherein the first and the second aqueous solutions are combined in the presence of finely divided tetrahydro-3,5-dimethyl-1,3,5-thiadiazine-2-thione.

4. The process as claimed in claim 1, wherein the first aqueous solution additionally comprises an alkylenediamine and/or reaction products thereof with carbon disulfide.

5. The process as claimed in claim 4, wherein the first aqueous solution comprises alkylenediamine, N-aminoalkyldithiocarbamate and alkylene-N,N'-bis (dithiocarbamate) in a molar ratio of 1:0.5:0.5 to 1:10:10.

6. The process as claimed in claim 1, wherein the first aqueous solution is obtained by reacting an aqueous solution of methylamine with a stoichiometric excess of carbon disulfide and removing the unreacted carbon disulfide to less than 0.5% by weight based on the aqueous solution.

7. The process as claimed in claim 6, wherein the aqueous solution for removing the unreacted carbon disulfide is passed through an apparatus with coalescence-enhancing elements and the coalesced carbon disulfide is phase separated off.

8. The process as claimed in claim 1, wherein the first and the second aqueous solutions are combined in the presence of a chelating agent for iron ions.

9. The process as claimed in claim 6, wherein the aqueous N-methylamine solution used is an aqueous methylamine solution loaded with some carbon disulfide, which solution is obtained when the process waste air, which contains carbon disulfide, is scrubbed with an aqueous methylamine solution.

10. The process as claimed in claim 4, wherein the alkylenediamine used is an alkylenediamine loaded with some carbon disulfide, which alkylenediamine is obtained when the process waste air, which contains carbon disulfide, is scrubbed with an alkylenediamine or an aqueous solution thereof.

* * * * *